United States Patent [19]

Olefsky et al.

[11] Patent Number: 5,478,852

[45] Date of Patent: Dec. 26, 1995

[54] USE OF THIAZOLIDINEDIONE DERIVATIVES AND RELATED ANTIHYPERGLYCEMIC AGENTS IN THE TREATMENT OF IMPAIRED GLUCOSE TOLERANCE IN ORDER TO PREVENT OR DELAY THE ONSET OF NONINSULIN-DEPENDENT DIABETES MELLITUS

[75] Inventors: Jerrold Olefsky, Solano Beach, Calif.; Tammy Antonucci, Mequon, Wis.; Dean Lockwood, Ann Arbor; Rebecca Norris, Kewadin, both of Mich.

[73] Assignee: Sankyo Company, Limited, Tokyo, Japan

[21] Appl. No.: 293,899

[22] Filed: Aug. 23, 1994

Related U.S. Application Data

[63] Continuation-in-part of Ser. No. 122,251, Sep. 15, 1993, abandoned.

[51] Int. Cl.$^6$ .......... A61K 31/44; A61K 31/425; A61K 31/41
[52] U.S. Cl. .......... 514/369; 514/252; 514/256; 514/342; 514/360; 514/375; 514/376
[58] Field of Search .......... 514/252, 256, 514/342, 360, 369, 375, 376

[56] References Cited

U.S. PATENT DOCUMENTS

| | | | |
|---|---|---|---|
| 4,287,200 | 9/1981 | Kawamatsu et al. | 424/270 |
| 4,340,605 | 7/1982 | Kawamatsu et al. | 424/263 |
| 4,438,141 | 3/1984 | Kawamatsu et al. | 424/248.51 |
| 4,444,779 | 4/1984 | Kawamatsu et al. | 424/263 |
| 4,461,902 | 7/1984 | Kawamatsu et al. | 548/183 |
| 4,572,912 | 2/1986 | Yoshioka et al. | 514/369 |
| 4,687,777 | 8/1987 | Meguro et al. | 514/342 |
| 4,703,052 | 10/1987 | Eggler et al. | 514/337 |
| 4,725,610 | 2/1988 | Meguro et al. | 514/369 |
| 4,873,255 | 10/1989 | Yoshioka et al. | 514/369 |
| 4,897,393 | 1/1990 | Iijima et al. | 514/233.8 |
| 4,897,405 | 1/1990 | Alessi et al. | 514/360 |
| 4,918,091 | 4/1990 | Cantello et al. | 514/369 |
| 4,948,900 | 8/1990 | Iijima et al. | 548/183 |
| 5,002,953 | 3/1991 | Hindley | 514/275 |
| 5,061,717 | 10/1991 | Clark et al. | 514/342 |
| 5,120,754 | 6/1992 | Clark et al. | 514/369 |
| 5,132,317 | 7/1992 | Cantello et al. | 514/369 |
| 5,194,443 | 3/1993 | Hindley | 514/367 |
| 5,223,522 | 6/1993 | Clark et al. | 514/369 |
| 5,232,925 | 8/1993 | Hindley | 514/272 |
| 5,260,445 | 11/1993 | Hindley et al. | 548/183 |

FOREIGN PATENT DOCUMENTS

| | | |
|---|---|---|
| 4-69383 | 3/1992 | Japan . |
| WO89/08651 | 9/1989 | WIPO . |
| WO91/07107 | 5/1991 | WIPO . |
| WO91/12003 | 8/1991 | WIPO . |
| WO92/02520 | 2/1992 | WIPO . |
| WO94/01433 | 1/1994 | WIPO . |

OTHER PUBLICATIONS

Saad et al, The New England Journal of Medicine, vol. 319, No. 23 (Dec. 8, 1988) pp. 1500–1506.
*Japan Diabetic Society*, vol. 31, Supplement 1, (May 1988) Abstracts VII–7 and 207.
Horikoshi et al, "Pharmacological Profile of CS–045, A New Orally Effective Antidiabetic Agent in Insulin Resistant Animal Models", (May 1988), *Poster Session*, vol. 37, Supplement 1, (ADA) New Orleans.
Anderson et al, "The Vasodilator Action of Insulin, Implications for the Insulin Hypothesis of Hypertension", *Hypertension*, vol. 21, No. 2 (Feb. 1993), pp. 136–141.
Baron et al, "Skeletal Muscle Blood Flow, A Possible Link Between Insulin Resistance and Blood Pressure", (Feb. 1993), pp. 129–135, *Hypertension*, vol. 21, No. 2.
Fujiwara et al, "Characterization of New Oral Antidiabetic Agent CS–045, Studies in KK and ob/ob Mice and Zucker Fatty Rats", (Nov. 1988), pp. 1549–1558, *Diabetes*, vol. 37.

*Primary Examiner*—Richard L. Raymond
*Attorney, Agent, or Firm*—Frishauf, Holtz, Goodman, Langer & Chick

[57] ABSTRACT

Novel methods of using thiazolidinone derivatives and related antihyperglycemic agents to treat populations experiencing impaired glucose intolerance in order to prevent or delay the onset of noninsulin-dependent diabetes mellitus (NIDDM) and complications arising therefrom are disclosed.

23 Claims, No Drawings

USE OF THIAZOLIDINEDIONE DERIVATIVES AND RELATED ANTIHYPERGLYCEMIC AGENTS IN THE TREATMENT OF IMPAIRED GLUCOSE TOLERANCE IN ORDER TO PREVENT OR DELAY THE ONSET OF NONINSULIN-DEPENDENT DIABETES MELLITUS

CROSS-REFERENCE TO RELATED APPLICATION

This is a continuation-in-part of U.S. application Ser. No. 08/122251 filed Sep. 15, 1993 now abandoned.

FIELD OF THE INVENTION

The present invention pertains to a number of compounds which can be used to treat impaired glucose tolerance in order to prevent or delay the onset of noninsulin-dependent diabetes mellitus (NIDDM). More specifically, the present invention involves in one embodiment administering to a patient certain known thiazolidinedione derivatives and related antihyperglycemic agents which reduce fasting insulin levels and return normal glucose tolerance to an individual, thus preventing or delaying the onset of NIDDM or complications resulting therefrom.

BACKGROUND

Diabetes is one of the most prevalent chronic disorders worldwide with significant personal and financial costs for patients and their families, as well as for society. Different types of diabetes exist with distinct etiologies and pathogeneses. For example, diabetes mellitus is a disorder of carbohydrate metabolism, characterized by hyperglycemia and glycosuria and resulting from inadequate production or utilization of insulin.

Diabetes mellitus often develops from certain at risk populations, one such population is individuals with impaired glucose tolerance (IGT). Impaired glucose tolerance is a condition intermediate between frank, noninsulin-dependent diabetes mellitus and normal glucose tolerance in which the affected person's postprandial glucose response is abnormal as assessed by 2-hour postprandial plasma glucose levels. This IGT population progresses to a certain form of diabetes mellitus, specifically noninsulin-dependent diabetes mellitus (NIDDM).

NIDDM or otherwise referred to as Type II diabetes is the form of diabetes mellitus which occurs predominantly in adults in whom adequate production of insulin is available for use, yet a defect exists in insulin-mediated utilization and metabolism of glucose in peripheral tissues. It has been shown that for some people with diabetes a genetic predisposition results in a mutation in the gene(s) coding for insulin and/or the insulin receptor and/or insulin-mediated signal transduction factor(s), thereby resulting in ineffective insulin and/or insulin-mediated effects thus impairing the utilization or metabolism of glucose. The population with impaired glucose tolerance progresses to NIDDM at a rate of 5% to 10% of cases per year.

Failure to treat NIDDM can result in mortality due to cardiovascular disease and in other diabetic complications including retinopathy, nephropathy, and peripheral neuropathy. For many years treatment of NIDDM has involved a program aimed at lowering blood sugar with a combination of diet and exercise. Alternatively, treatment of NIDDM involved oral hypoglycemic agents, such as sulfonylureas alone or in combination with insulin injections. Recently, alpha-glucosidase inhibitors, such as acarbose, have been shown to be effective in reducing the postprandial rise in blood glucose (Lefevre, et al., *Drugs* 1992;44: 29–38). In Europe and Canada another treatment used primarily in obese diabetics is metformin, a biguanide.

In any event, what is required is a method of treating populations experiencing impaired glucose tolerance in order to prevent or delay the onset of NIDDM thereby bringing relief of symptoms, improving the quality of life, preventing acute and long-term complications, reducing mortality and treating accompanying disorders of those at risk for NIDDM. The methods of using the disclosed compounds for treating populations experiencing impaired glucose tolerance to prevent or delay the onset of NIDDM as taught herein meet these objectives.

Compounds useful for practicing the present invention, and methods of making these compounds are known. Some of these compounds are disclosed in WO 91/07107; WO 92/02520; WO 94/01433; WO 89/08651; JP Kokai 69383/92; U.S. Pat. Nos. 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; and 5,260,445. The active compounds disclosed in these publications are useful as therapeutic agents for the treatment of diabetes, hyperglycemia, hypercholesterolemia, and hyperlipidemia. The disclosure of these publications are incorporated herein by reference in particular with respect to the active compounds disclosed therein, and methods of preparation thereof. These compounds are useful for the treatment of impaired glucose tolerance (IGI) in order to prevent or delay onset of NIDDM and complications resulting therefrom, in accordance with the present invention.

There is no disclosure in the above-identified references to use the compounds identified in this present application in the treatment of populations experiencing impaired glucose tolerance in order to prevent or delay the onset of NIDDM and complications resulting therefrom.

SUMMARY OF THE INVENTION

The present invention provides a method for the treatment of impaired glucose tolerance in order to prevent or delay the onset of NIDDM. It is known that persons with impaired glucose tolerance have a much higher rate of progression to NIDDM than persons with normal glucose tolerance. Saad, et al., *New Engl J Med* 1988; 319:1500–6. If impaired glucose tolerance can be normalized, it is likely that the progression to NIDDM will be delayed or prevented in this population.

Compounds useful for practicing the present invention reduce fasting insulin levels, improve insulin sensitivity, and return glucose tolerance to the normal range for many individuals. As agents having the aforementioned effects (in the return of glucose tolerance), the compounds of the following formulas are useful in prophylactically treating individuals to prevent or delay the onset of NIDDM.

Accordingly, the present invention is the use of compounds of Formula I

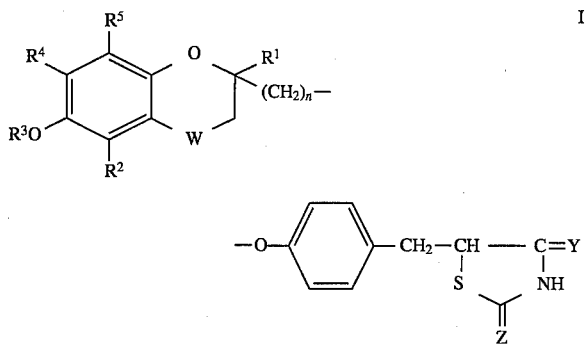

wherein $R^1$ and $R^2$ are the same or different and each represents a hydrogen atom or a $C_1-C_5$ alkyl group;

$R^3$ represents a hydrogen atom, a $C_1-C_6$ aliphatic acyl group, an alicyclic acyl group, an aromatic acyl group, a heterocyclic acyl group, an araliphatic acyl group, a ($C_1-C_6$ alkoxy)carbonyl group, or an aralkyloxycarbonyl group;

$R^4$ and $R^5$ are the same or different and each represents a hydrogen atom, a $C_1-C_5$ alkyl group or a $C_1-C_5$ alkoxy group, or $R^4$ and $R^5$ together represent a $C_1-C_5$ alkylenedioxy group;

n is 1, 2, or 3;

W represents the —$CH_2$—, >CO, or CH—$OR^6$ group (in which $R^6$ represents any one of the atoms or groups defined for $R^3$ and may be the same as or different from $R^3$); and Y and Z are the same or different and each represents an oxygen atom or an imino (=NH) group;

and pharmaceutically acceptable salts thereof.

The present invention is also the use of compounds of the Formula II

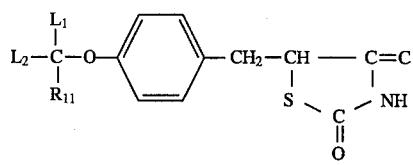

wherein $R_{11}$ is substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula

wherein $R_{13}$ and $R_{14}$ are the same or different and each is lower alkyl or $R_{13}$ and $R_{14}$ are combined to each other either directly or as interrupted by a heteroatom selected from the group consisting of nitrogen, oxygen, and sulfur to form a 5- or 6-membered ring; wherein $R_{12}$ means a bond or a lower alkylene group; and wherein $L_1$ and $L_2$ are the same or different and each is hydrogen or lower alkyl or $L_1$ and $L_2$ are combined to form an alkylene group; or a pharmaceutically acceptable salt thereof.

The present invention is also the use of compounds of the Formula III

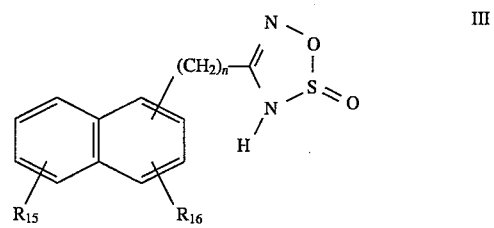

wherein $R_{15}$ and $R_{16}$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro, or halogen substituted benzyloxy; n is 0 to 4 and the pharmaceutically acceptable salts thereof.

The present invention is also directed to the use of compounds of the Formula IV

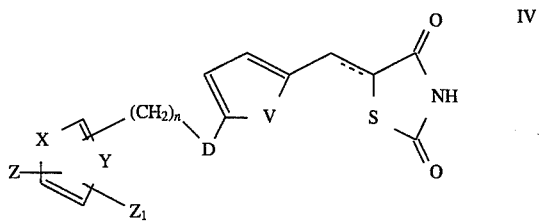

wherein the dotted line represents a bond or no bond;

V is —CH=CH—, —N=CH—, —CH=N— or S;

D is $CH_2$, CHOH, CO, C=$NOR_{17}$ or CH=CH;

X is S, O, $NR_{18}$, —CH=N or —N=CH;

Y is CH or N;

Z is hydrogen, ($C_1-C_7$) alkyl ($C_1-C_7$)cycloalkyl, phenyl, naphthyl, pyridyl, furyl, thienyl, or phenyl mono- or disubstituted with the same or different groups which are ($C_1-C_3$)alkyl, trifluoromethyl, ($C_1-C_3$)alkoxy, fluoro, chloro, or bromo;

$Z_1$ is hydrogen or ($C_1-C_3$)alkyl;

$R_{17}$ and $R_{18}$ are each independently hydrogen or methyl; and n is 1, 2, or 3;

the pharmaceutically acceptable cationic salts thereof; and the pharmaceutically acceptable acid addition salts thereof when the compound contains a basic nitrogen.

The present invention is also directed to the use of compounds of the Formula V

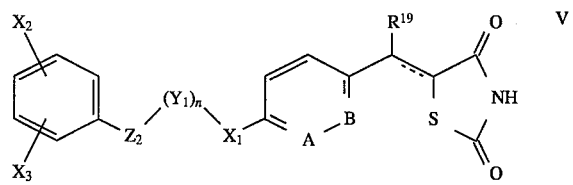

wherein the dotted line represents a bond or no bond;

A and B are each independently CH or N, with the proviso that when A or B is N, the other is CH;

$X_1$ is S, SO, $SO_2$, $CH_2$, CHOH, or CO;

n is 0 or 1;

$Y_1$ is $CHR_{20}$ or $R_{21}$, with the proviso that when n is 1 and $Y_1$ is $NR_{21}$, $X_1$ is $SO_2$ or CO;
$Z_2$ is $CHR_{22}$, $CH_2CH_2$, CH=CH,

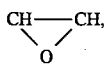

$OCH_2$, $SCH_2$, $SOCH_2$ or $SO_2CH_2$;

$R_{19}$, $R_{20}$, $R_{21}$, and $R_{22}$ are each independently hydrogen or methyl; and $X_2$ and $X_3$ are each independently hydrogen, methyl, trifluoromethyl, phenyl, benzyl, hydroxy, methoxy, phenoxy, benzyloxy, bromo, chloro, or fluoro;

a pharmaceutically acceptable cationic salt thereof; or a pharmaceutically acceptable acid addition salt thereof when A or B is N.

The present invention also relates to the use of compounds of the Formula VI

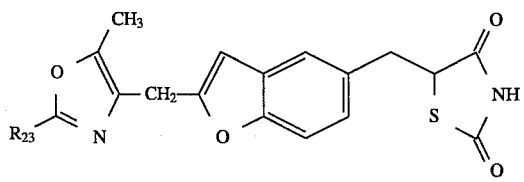

or a pharmaceutically acceptable salt thereof wherein $R_{23}$ is alkyl of 1 to 6 carbon atoms, cycloalkyl of 3 to 7 carbon atoms, phenyl or mono- or di-substituted phenyl wherein said substituents are independently alkyl of 1 to 6 carbon atoms, alkoxy of 1 to 3 carbon atoms, halogen, or trifluoromethyl.

The present invention also provides the use of a compound of Formula VII

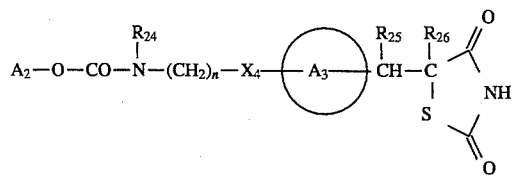

or a tautomeric form thereof and/or a pharmaceutically acceptable salt thereof, and/or a pharmaceutically acceptable solvate thereof, wherein:

$A_2$ represents an alkyl group, a substituted or unsubstituted aryl group, or an aralkyl group wherein the alkylene or the aryl moiety may be substituted or unsubstituted;

$A_3$ represents a benzene ring having in total up to 3 optional substituents;

$R_{24}$ represents a hydrogen atom, an alkyl group, an acyl group, an aralkyl group wherein the alkyl or the aryl moiety may be substituted or unsubstituted, or a substituted or unsubstituted aryl group; or $A_2$ together with $R_{24}$ represents substituted or unsubstituted $C_{2-3}$ polymethylene group, optional substituents for the polymethylene group being selected from alkyl or aryl or adjacent substituents together with the methylene carbon atoms to which they are attached form a substituted or unsubstituted phenylene group;

$R_{25}$ and $R_{26}$ each represent hydrogen, or $R_{25}$ and $R_{26}$ together represent a bond;

$X_4$ represents O or S; and n represents an integer in the range of from 2 to 6.

The present invention also provides the use of a compound of Formula VIII

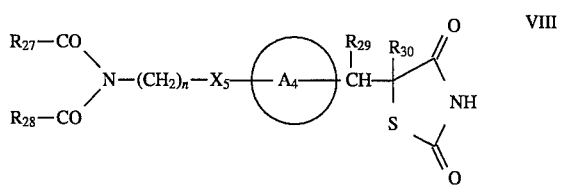

or a tautomeric form thereof and/or a pharmaceutically acceptable salt thereof, and/or a pharmaceutically acceptable solvate therefor, wherein:

$R_{27}$ and $R_{28}$ each independently represent an alkyl group, a substituted or unsubstituted aryl group, or an aralkyl group being substituted or unsubstituted in the aryl or alkyl moiety; or $R_{27}$ together with $R_{28}$ represents a linking group, the linking group consisting of an optionally substituted methylene group and either a further optionally substituted methylene group or an O or S atom, optional substituents for the said methylene groups being selected from alkyl-, aryl, or aralkyl, or substituents of adjacent methylene groups together with the carbon atoms to which they are attached form a substituted or unsubstituted phenylene group;

$R_{29}$ and $R_{30}$ each represent hydrogen, or $R_{29}$ and $R_{30}$ together represent a bond;

$A_4$ represents a benzene ring having in total up to 3 optional substituents;

$X_5$ represents O or S; and n represents an integer in the range of from 2 to 6.

The present invention also provides the use of a compound of Formula IX

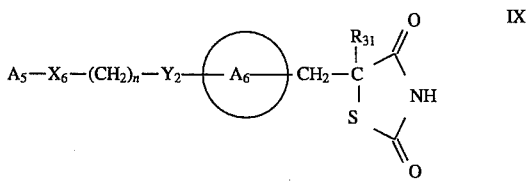

or a tautomeric form thereof and/or a pharmaceutically acceptable salt thereof, and/or a pharmaceutically acceptable solvate thereof, wherein:

$A_5$ represents a substituted or unsubstituted aromatic heterocyclyl group;

$A_6$ represents a benzene ring having in total up to 5 substituents;

$X_6$ represents O, S, or $NR_{32}$ wherein $R_{32}$ represents a hydrogen atom, an alkyl group, an acyl group, an aralkyl group, wherein the aryl moiety may be substituted or unsubstituted, or a substituted or unsubstituted aryl group;

$Y_2$ represents O or S;

$R_{31}$ represents an alkyl, aralkyl, or aryl group; and n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen, sulphur, or nitrogen.

Favored aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2, or 3 heteroatoms, especially 1 or 2, selected from oxygen, sulphur, or nitrogen.

Suitable values for $A_5$ when it represents a 5-membered aromatic heterocyclyl group include thiazolyl and oxazoyl, especially oxazoyl.

Suitable values for $A_5$ when it represents a 6-membered aromatic heterocyclyl group include pyridyl or pyrimidinyl.

Suitable $R_{31}$ represents an alkyl group, in particular a $C_{1-6}$ alkyl group, for example a methyl group. Preferably, $A_5$ represents a moiety of formula (a), (b), or (c):

$$R_{33}\diagdown\kern-0.5em\diagup N\diagdown\kern-0.5em\diagup \atop R_{34}\diagup\kern-0.5em\diagdown X_7\diagup \qquad (a)$$

$$R_{33}\diagdown\kern-0.5em\diagup N\diagdown\kern-0.5em\diagup \atop R_{34}\diagup\kern-0.5em\diagdown N \qquad (b)$$

$$R_{33}\diagdown\kern-0.5em\diagup \diagdown\kern-0.5em\diagup \atop R_{34}\diagup\kern-0.5em\diagdown N\diagdown \qquad (c)$$

wherein:

$R_{33}$ and $R_{34}$ each independently represents a hydrogen atom, an alkyl group, or a substituted or unsubstituted aryl group or when $R_{33}$ and $R_{34}$ are each attached to adjacent carbon atoms, then $R_{33}$ and $R_{34}$ together with the carbon atoms to which they are attached form a benzene ring wherein each carbon atom represented by $R_{33}$ and $R_{34}$ together may be substituted or unsubstituted; and in the moiety of Formula (a), $X_7$ represents oxygen or sulphur.

In one favored aspect $R_{33}$ and $R_{34}$ together represent a moiety of Formula (d):

$$R_{35}\diagdown\kern-0.5em\diagup \diagdown \atop R_{36}\diagup\kern-0.5em\diagdown \diagup \qquad (d)$$

wherein $R_{35}$ and $R_{36}$ each independently represent hydrogen, halogen, substituted or unsubstituted alkyl, or alkoxy.

The present invention also provides for the use of compounds for Formula X $$A_7-X_8-(CH_2)_n-Y_3-\!\!\bigcirc\!\!A_8\!\!\bigcirc\!\!-\underset{\underset{S}{|}}{\overset{\overset{R_{37}}{|}}{CH}}-\underset{\underset{\diagdown C(=O)}{}}{\overset{\overset{R_{38}}{|}}{C}}\diagup\overset{O}{\diagdown}NH \qquad X$$

or a tautomeric form thereof and/or a pharmaceutically acceptable salt thereof, and/or a pharmaceutically acceptable solvate thereof, wherein:

$A_7$ represents a substituted or unsubstituted aryl group;

$A_8$ represents a benzene ring having in total up to 5 substituents;

$X_8$ represents O, S, or $NR_{39}$ wherein $R_{39}$ represents a hydrogen atom, an alkyl group, an acyl group, an aralkyl group, wherein the aryl moiety may be substituted or unsubstituted, or a substituted or unsubstituted aryl group;

$Y_3$ represents O or S;

$R_{37}$ represents hydrogen;

$R_{38}$ represents hydrogen or an alkyl, aralkyl, or aryl group or $R_{37}$ together with $R_{38}$ represents a bond; and n represents an integer in the range of from 2 to 6.

The present invention is also directed to the use of compounds of the Formula $$A^1-\underset{\underset{}{|}}{\overset{\overset{R^1}{|}}{N}}-(CH_2)_n-O-\!\!\bigcirc\!\!A^2\!\!\bigcirc\!\!-CH_2-CH\diagup\overset{O}{\diagdown}NH \qquad XI$$

or a tautomeric form thereof and/or a pharmaceutically acceptable salt thereof, and/or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to five substituents; and n represents an integer in the range of from 2 to 6.

Suitable aromatic heterocyclyl groups include substituted or unsubstituted, single or fused ring aromatic heterocyclyl groups comprising up to 4 hereto atoms in each ring selected from oxygen, sulphur or nitrogen.

Favoured aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2 or 3 heteroatoms, especially 1 to 2, selected from oxygen, sulphur or nitrogen.

Suitable values for $A^1$ when it represents a 5-membered aromatic heterocyclyl group include thiazoylyl and oxazolyl, especially oxazolyl.

Suitable values for $A^1$ when it represents a 6-membered aromatic heterocyclyl group include pyridyl or pyrimidinyl.

Preferably, $A^1$ represents a moiety of formula (a), (b) or (c):

$$R^4\diagdown\kern-0.5em\diagup N\diagdown\kern-0.5em\diagup \atop R^5\diagup\kern-0.5em\diagdown X\diagup \qquad (a)$$

$$R^4\diagdown\kern-0.5em\diagup N\diagdown\kern-0.5em\diagup \atop R^5\diagup\kern-0.5em\diagdown N \qquad (b)$$

$$R^4\diagdown\kern-0.5em\diagup \diagdown\kern-0.5em\diagup \atop R^5\diagup\kern-0.5em\diagdown N\diagdown \qquad (c)$$

wherein:

$R^4$ and $R^5$ each independently represents a hydrogen atom, an alkyl group or a substituted or unsubstituted aryl group or when $R^4$ and $R^5$ are each attached to adjacent carbon atoms, then $R^4$ and $R^5$ together with the carbon atoms to which they are attached form a benzene ring wherein each carbon atom represented by $R^4$ and $R^5$ together may be substituted or unsubstituted; and in the moiety of formula (a) X represents oxygen or sulphur.

The present invention is also directed to the use of compounds of the Formulas

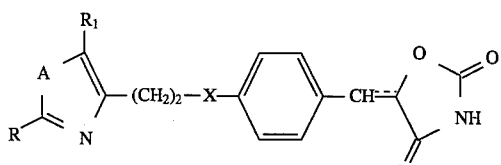

XII

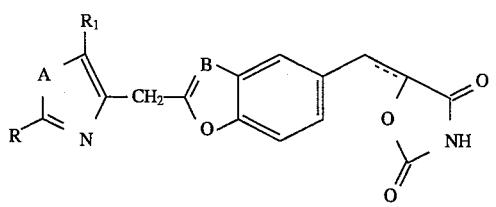

XIII or a pharmaceutically acceptable salt thereof wherein the dotted line represents a bond or no bond; R is cycloalkyl of three to seven carbon atoms, naphthyl, thienyl, furyl, phenyl or substituted phenyl wherein said substituent is alkyl of one to three carbon atoms, alkoxy of one to three carbon atoms, trifluoromethyl, chloro, fluoro or bis(trifluoromethyl); $R_1$ is alkyl of one to three carbon atoms; X is O or C=O; A is O or S; and B is N or CH.

A preferred group of compounds are those of formula XI wherein the dotted line represents no bond, $R_1$ is methyl, X is O and A is O. Especially preferred within this group are the compounds where R is phenyl, 2-naphthyl and 3,5-bis(trifluoromethyl)phenyl.

A second group of preferred compounds are those of formula XII wherein the dotted line represents no bond, $R_1$ is methyl and A is O. Especially preferred within this group are compounds where B is CH and R is phenol, p-tolyl, m-tolyl, cyclohexyl and 2-naphthyl. Also especially preferred is the compound where B is N and R is phenyl.

A still further embodiment of the present invention is the use of a pharmaceutical composition for administering an effective amount of a compound of the preceding Formulas I through XIII along with a pharmaceutically acceptable carrier in unit dosage form in the treatment methods mentioned above.

DETAILED DESCRIPTION OF THE PREFERRED EMBODIMENTS

The compounds used in the treatment methods of the invention, which are 5-[4-(chromoanalkoxy)benzyl]-thiazolidene derivatives, may be represented by the Formulas (Ia), (Ib), and (Ic)

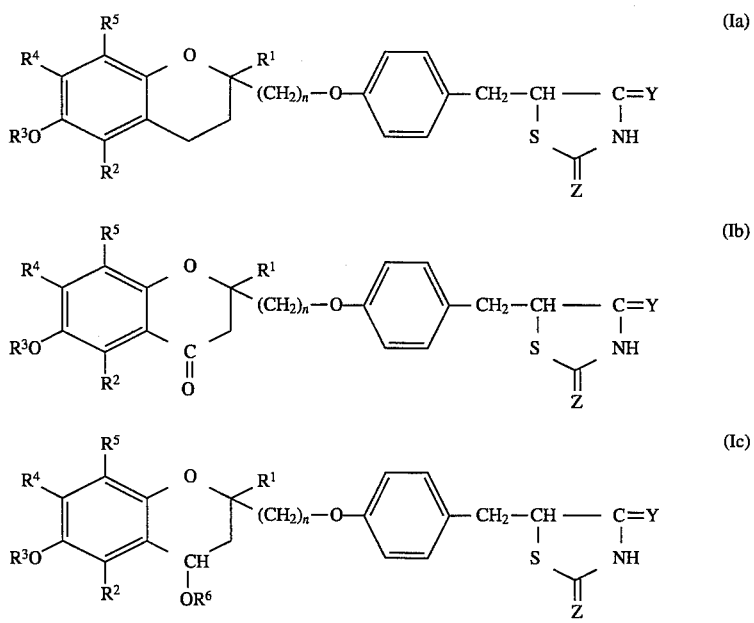

(in which $R^1$, $R^2$, $R^3$, $R^4$, $R^5$, $R^6$, n, Y, and Z are as defined above) and include pharmaceutically acceptable salts thereof.

In the compounds of the invention where $R^1$ or $R^2$ represents an alkyl group, this may be a straight or branched chain alkyl group having having from 1 to 5 carbon atoms and is preferably a primary or secondary alkyl group, for example the methyl, ethyl, propyl, isopropyl, butyl, isobutyl, pentyl, or isopentyl group.

Where $R^3$, $R^6$, or $R^{6'}$ represents an aliphatic acyl group, this preferably has from 1 to 6 carbon atoms and may include one or more carbon-carbon double or triple bonds.

Examples of such groups include the formyl, acetyl, propionyl, butyryl, isobutyryl, pivaloyl, hexanoyl, acryloyl, methacryloyl, and crotonyl groups.

Where $R^3$, $R^6$, or $R^{6'}$ represents an alicyclic acyl group, it is preferably a cyclopentanecarbonyl, cyclohexanecarbonyl, or cycloheptanecarbonyl group.

Where $R^3$, $R^6$, or $R^{6'}$ represents an aromatic acyl group, the aromatic moiety thereof may optionally have one or more substituents (for example, nitro, amino, alkylamino, dialkylamino, alkoxy, halo, alkyl, or hydroxy substituents); examples of such aromatic acyl groups included the benzoyl, p-nitrobenzoyl, m-fluorobenzoyl, o-chlorobenzoyl, p-aminobenzoyl, m-(dimethylamino)benzoyl, o-methoxybenzoyl, 3,4-dichlorobenzoyl, 3,5-di-t-butyl-4-hydroxybenzoyl, and 1-naphthoyl groups.

Where $R^3$, $R^6$, or $R^{6'}$ represents a heterocyclic acyl group, the heterocyclic moiety thereof preferably has one or more, preferably one, oxygen, sulfur, or nitrogen hetero atoms and has from 4 to 7 ring atoms; examples of such heterocyclic acyl groups include the 2-furoyl, 3-thenoyl, 3-pyridinecarbonyl (nicotinoyl), and 4-pyridinecarbonyl groups.

Where $R^3$, $R^6$, or $R^{6'}$ represents an araliphatic acyl group, the aliphatic moiety thereof may optionally have one or more carbon-carbon double or triple bonds and the aryl moiety thereof may optionally have one or more substituents (for example, nitro, amino, alkylamino, dialkylamino, alkoxy, halo, alkyl, or hydroxy substituents); examples of such araliphatic acyl groups include the phenylacetyl, p-chlorophenylacetyl, phenylpropionyl, and cinnamoyl groups.

Where $R^3$, $R^6$, or $R^{6'}$ represents a ($C_1$–$C_6$ alkoxy)carbonyl group, the alkyl moiety thereof may be any one of those alkyl groups as defined for $R^1$ and $R^2$, but is preferably a methyl or ethyl group, and the alkoxycarbonyl group represented by $R^3$, $R^6$, or $R^{6'}$ is therefore preferably a methoxycarbonyl or ethoxycarbonyl group.

Where $R^3$, $R^6$, or $R^{6'}$ represents an aralkyloxycarbonyl group, the aralkyl moiety thereof may be any one of those included within the araliphatic acyl group represented by $R^3$, $R^6$, or $R^{6'}$, but is preferably a benzyloxycarbonyl group.

Where $R^4$ and $R^5$ represent alkyl groups, they may be the same or different and may be straight or branched chain alkyl groups. They preferably have from 1 to 5 carbon atoms and examples include the methyl, ethyl, propyl, isopropyl, butyl, isobutyl, t-butyl, pentyl, and isopentyl groups.

Where $R^4$ and $R^5$ represent alkoxy groups, these may be the same or different and may be straight or branched chain groups, preferably having from 1 to 4 carbon atoms. Examples include the methoxy, ethoxy, propoxy, isopropoxy, and butoxy groups. Alternatively, $R^4$ and $R^5$ may together represent a $C_1$–$C_4$ alkylenedioxy group, more preferably a methylenedioxy or ethylenedioxy group.

Preferred classes of compounds of Formula I are as follows:

(1) Compounds in which $R^3$ represents a hydrogen atom, a $C_1$–$C_6$ aliphatic acyl group, an aromatic acyl group, or a heterocyclic acyl group.

(2) Compounds in which Y represents an oxygen atom; $R^1$ and $R^2$ are the same or different and each represents a hydrogen atom or a $C_1$–$C_5$ alkyl group; $R^3$ represents a hydrogen atom, a $C_1$–$C_6$ aliphatic acyl group, an aromatic acyl group, or a pyridinecarbonyl group; and $R^4$ and $R^5$ are the same or different and each represents a hydrogen atom, a $C_1$–$C_5$ alkyl group, or a $C_1$ or $C_2$ alkoxy group.

(3) Compounds as defined in (2) above, in which: $R^1$, $R^2$, $R^4$, and $R^5$ are the same or different and each represents a hydrogen atom or a $C_1$–$C_5$ alkyl group; n is 1 or 2; and W represents the —$CH_2$— or >CO group.

(4) Compounds as defined in (3) above, in which $R^3$ represents a hydrogen atom, a $C_1$–$C_5$ aliphatic acyl group, a benzoyl group, or a nicotinyl group.

(5) Compounds as defined in (4) above, in which: $R^1$ and $R^4$ are the same or different and each represents a $C_1$–$C_5$ alkyl group; $R^2$ and $R^5$ are the same or different and each represents the hydrogen atom or the methyl group; and $R^3$ represents a hydrogen atom or a $C_1$–$C_4$ aliphatic acyl group.

(6) Compounds in which: W represents the —$CH_2$— or >CO group; Y and Z both represent oxygen atoms; n is 1 or 2; $R^1$ and $R^4$ are the same or different and each represents a $C_1$–$C_4$ alkyl group; $R^2$ and $R^5$ are the same or different and each represents the hydrogen atom or the methyl group; and $R^3$ represents a hydrogen atom or a $C_1$–$C_4$ aliphatic acyl group.

(7) Compounds as defined in (6) above, in which n is 1.

(8) Compounds as defined in (6) or (7) above, in which W represents the —$CH_2$— group.

Preferred compounds among the compounds of Formula I are those wherein:

$R^1$ is a $C_1$–$C_4$ alkyl group, more preferably a methyl or isobutyl group, most preferably a methyl group;

$R^2$ is a hydrogen atom or a $C_1$–$C_4$ alkyl group, preferably a hydrogen atom, or a methyl or isopropyl group, more preferably a hydrogen atom or a methyl group, most preferably a methyl group;

$R^3$ is a hydrogen atom, a $C_1$–$C_4$ aliphatic acyl group, an aromatic acyl group or a pyridinecarbonyl group, preferably a hydrogen atom, or an acetyl, butyryl, benzoyl, or nicotinyl group, more preferably a hydrogen atom or an acetyl, butyryl or benzoyl group, most preferably a hydrogen atom or an acetyl group;

$R^4$ is a hydrogen atom, a $C_1$–$C_4$ alkyl group or a $C_1$ or $C_2$ alkoxy group, preferably a methyl, isopropyl, t-butyl, or methoxy group, more preferably a methyl or t-butyl group, most preferably a methyl group;

$R^5$ is a hydrogen atom, a $C_1$–$C_4$ alkyl group or a $C_1$ or $C_2$ alkoxy group, preferably a hydrogen atom, or a methyl or methoxy group, more preferably a hydrogen atom or a methyl group, and most preferably a methyl group;

n is 1 or 2, preferably 1;

Y is an oxygen atom;

Z is an oxygen atom or an imino group, most preferably an oxygen atom; and

W is a —$CH_2$— or >C=O group, preferably a —$CH_2$ group.

Referring to the general Formula II, the substituents may be any from 1 to 3 selected from nitro, amino, alkylamino, dialkylamino, alkoxy, halo, alkyl, or hydroxy, the aromatic acyl group may be benzoyl and naphthoyl. The alkyl group $R_{11}$ may be a straight chain or branched alkyl of 1 to 10 carbon atoms, such as methyl, ethyl, n-propyl, i-propyl, n-butyl, i-butyl, t-butyl, n-pentyl, i-pentyl, n-hexyl, n-heptyl, n-octyl, n-nonyl, and n-decyl; the cycloalkyl group $R_{11}$ may be a cycloalkyl group of 3 to 7 carbon atoms, such as cyclopropyl, cyclopentyl, cyclohexyl, and cycloheptyl; and the phenylalkyl group $R_{11}$ may be a phenylalkyl group of 7 to 11 carbon atoms such as benzyl and phenethyl. As examples of the heterocyclic group $R_{11}$ may be mentioned 5- or 6-membered groups each including 1 or 2 hetero-atoms selected from among nitrogen, oxygen, and sulfur, such as pyridyl, thienyl, furyl, thiazolyl, etc. When $R_{11}$ is

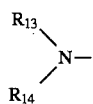

the lower alkyls $R_{13}$ and $R_{14}$ may each be a lower alkyl of 1 to 4 carbon atoms, such as methyl, ethyl, n-propyl, i-propyl, and n-butyl. When $R_{13}$ and $R_{14}$ are combined to each other to form a 5- or 6-membered heterocyclic group as taken together with the adjacent N atom, i.e., in the form of

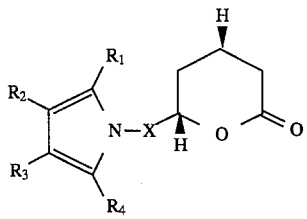

this heterocyclic group may further include a heteroatom selected from among nitrogen, oxygen, and sulfur as exemplified by piperidino, morpholino, pyrrolidino, and piperazino. The lower alkylene group $R_{12}$ may contain 1 to 3 carbon atoms and thus may be, for example, methylene, ethylene, or trimethylene. The bond $R_{12}$ is equivalent to the symbol "—", ".", or the like which is used in chemical structural formulas, and when $R_{12}$ represents such a bond, the compound of general Formula II is represented by the following general Formula II(a)

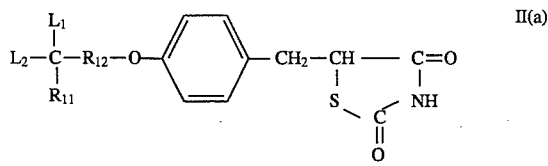

Thus, when $R_{12}$ is a bond, the atoms adjacent thereto on both sides are directly combined together. As examples of the lower alkyls $L_1$ and $L_2$, there may be mentioned lower alkyl groups of 1 to 3 carbon atoms, such as methyl and ethyl. The alkylene group formed as $L_1$ and $L_2$ are joined together is a group of the formula —$(CH_2)_n$— [where n is an integer of 2 to 6]. The cycloalkyl, phenylalkyl, phenyl, and heterocyclic groups mentioned above, as well as said heterocyclic group

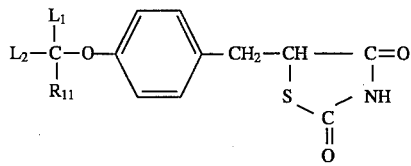

may have 1 to 3 substituents in optional positions on the respective rings. As examples of such substituents may be mentioned lower alkyls (e.g., methyl, ethyl, etc.), lower alkoxy groups (e.g., methoxy, ethoxy, etc.), halogens (e.g., chlorine, bromine, etc.), and hydroxyl. The case also falls within the scope of the general Formula II that an alkylenedioxy group of the formula —O—$(CH_2)_m$—O— [is an integer of 1 to 3], such as methylenedioxy, is attached to the two adjacent carbon atoms on the ring to form an additional ring.

The preferred compounds of Formula III are those wherein $R_{15}$ and $R_{16}$ are independently hydrogen, lower alkyl containing 1 to 6 carbon atoms, alkoxy containing 1 to 6 carbon atoms, halogen, ethynyl, nitrile, trifluoromethyl, vinyl, or nitro; n is 1 or 2 and the pharmaceutically acceptable salts thereof.

Preferred in Formula IV are compounds wherein the dotted line represents no bond, particularly wherein D is CO or CHOH. More preferred are compounds wherein V is —CH=CH—, —CH=N— or S and n is 2, particularly those compounds wherein X is O and Y is N, X is S and Y is N, X is S and Y is CH or X is —CH=N— and Y is CH. In the most preferred compounds X is O or S and Y is N forming an oxazol-4-yl, oxazol-5-yl, thiazol-4-yl, or thiazol-5-yl group; most particularly a 2-[(2-thienyl), (2-furyl), phenyl, or substituted phenyl]-5-methyl-4-oxazolyl group.

The preferred compounds in Formula V are:

a) those wherein the dotted line represents no bond, A and B are each CH, $X_1$ is CO, n is O, $R_{19}$ is hydrogen, $Z_2$ is $CH_2CH_2$ or CH=CH and $X_3$ is hydrogen, particularly when $X_2$ is hydrogen, 2-methoxy, 4-benzyloxy, or 4-phenyl;

b) those wherein A and B are each CH, $X_1$ is S or $SO_2$, n is O, $R_{19}$ is hydrogen, $Z_2$ is $CH_2CH_2$ and $X_3$ is hydrogen, particularly when $X_2$ is hydrogen or 4-chloro.

A preferred group of compounds is that of Formula VI wherein $R_{23}$ is $(C_1-C_6)$alkyl, $(C_3-C_7)$cycloalkyl, phenyl, halophenyl, or $(C_1-C_6)$alkylphenyl. Especially preferred within this group are the compounds where $R_{23}$ is phenyl, methylphenyl, fluorophenyl, chlorophenyl, or cyclohexyl.

When used herein with regard to Formulas VII through X, the term "aryl" includes phenyl and naphthyl, suitably phenyl, optionally substituted with up to 5, preferably up to 3, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

The term "halogen" refers to fluorine, chlorine, bromine, and iodine; preferably chlorine.

The terms "alkyl" and "alkoxy" relate to groups having straight or branched carbon chains, containing up to 12 carbon atoms.

Suitable alkyl groups are $C_{1-12}$ alkyl groups, especially $C_{1-6}$ alkyl groups, e.g., methyl, ethyl, n-propyl, iso-propyl, n-butyl, isobutyl, or tert-butyl groups.

Suitable substituents for any alkyl group include those indicated above in relation to the term "aryl".

Suitable substituents for any heterocyclyl group include up to 4 substituents selected from the group consisting of alkyl, alkoxy, aryl, and halogen or any 2 substituents on adjacent carbon atoms, together with the carbon atoms to which they are attached, may form an aryl group, preferably a benzene ring, and wherein the carbon atoms of the aryl group represented by the said 2 substituents may themselves be substituted or unsubstituted.

Specific examples of compounds of the present invention are given in the following list:

(+)-5-[[4-[(3,4-dihydro-6-hydroxy-2,5,7,8-tetramethyl-2H-1-benzopyran-2-yl)methoxy]phenyl]methyl]-2,4-thiazolidinedione: (troglitazone);

4-(2-naphthylmethyl)-1,2,3,5-oxathiadiazole-2-oxide;

5-[4-[2-[N-(benzoxazol-2-yl)-N-methylamino]ethoxy]benzyl]-5-methylthiazolidine-2,4-dione;

5-[4-[2-[2,4-dioxo-5-phenylthiazolidin-3-yl)ethoxy]benzyl] thiazolidine-2,4-dione;

5-[4-[2-[N-methyl-N-(phenoxycarbonyl)amino]ethoxy]benzyl]thiazolidine-2,4-dione;
5-[4-(2-phenoxyethoxy)benzyl]thiazolidine-2,4-dione;
5-[4-[2-(4-chlorophenyl)ethylsulfonyl]benzyl]thiazolidine-2,4-dione;
5-[4-[3-(5-methyl-2-phenyloxazol-4-yl)propionyl]benzyl]thiazolidine-2,4-dione;
5-[4-[(1-methylcyclohexyl)methoxy]benzyl]thiadiazolidine-2,4-dione: (ciglitazone);
5-[[4-(3-hydroxy-1-methylcyclohexyl)methoxy]benzyl]thiadiazolidine-2,4-dione;
5-[4-[2-(5-methyl-2-phenyloxazol-4-yl)ethoxyl]benzyl]thiadizolidione-2,4-dione;
5-[4-[2-(5-ethylpyridin-2-yl)ethoxyl]benzyl]thiadiazolidine-2,4-dione: (pioglitazone);
5-[(2-benzyl-2,3-dihydrobenzopyran)-5-ylmethyl]thiadiazoline-2,4-dione: (englitazone);
5-[[2-(2-naphthylmethyl)benzoxazol]-5-ylmethyl]thiadiazoline-2,4-dione;
5-[4-[2-(3-phenylureido)ethoxyl]benzyl]thiadiazoline-2,4-dione;
5-[4-[2-[N-(benzoxazol-2-yl)-N-methylamino]ethoxy]benzy]thiadiazoline-2,4-dione;
5-[4-[3-(5-methyl-2-phenyloxazol-4-yl)propionyl]benzyl]thiadiazoline-2,4-dione;
5-[2-(5-methyl-2-phenyloxazol-4-ylmethyl)benzofuran-5-ylmethyl]-oxazolidine-2,4-dione;
5-[4-[2-[N-methyl-N-(2-pyridyl)amino]ethoxy]benzyl]thiazolidine-2,4-dione; and
5-[4-[2-[N-(benzoxazol-2-yl)-N-methylamino]ethoxy]benzyl]-oxazolidine-2,4-dione.

As defined herein, "complications of NIDDM" is referred to as cardiovascular complications or several of the metabolic and circulatory disturbances that are associated with hyperglycemia, e.g., insulin resistance, hyperinsulinemia and/or hyperproinsulinemia, delayed insulin release, dyslipidemia, retinopathy, peripheral neuropathy, nephropathy, and hypertension.

The compounds of Formulas I through XIII are capable of further forming pharmaceutically acceptable base salts.

The compounds of Formulas I through XIII are capable of further forming both pharmaceutically acceptable acid addition and/or base salts. All of these forms are within the scope of the present invention.

Pharmaceutically acceptable acid addition salts of the compounds of Formulas I through XIII include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge S. M., et al., "Pharmaceutical Salts," *Journal of Pharmaceutical Science* 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner or as above. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *Journal of Pharmaceutical Science* 1977;66:1–19).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner or as above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention. Certain of the compounds of the present invention possess one or more chiral centers and each center may exist in different configurations. The compounds can, therefore, form stereoisomers. Although these are all represented herein by a limited number of molecular formulas, the present invention includes the use of both the individual, isolated isomers and mixtures, including racemates, thereof. Where stereospecific synthesis techniques are employed or optically active compounds are employed as starting materials in the preparation of the compounds, individual isomers may be prepared directly; on the other hand, if a mixture of isomers is prepared, the individual isomers may be obtained by conventional resolution techniques, or the mixture may be used as it is, without resolution.

Furthermore, the thiazolidene or oxazolidene part of the compounds of Formulas I through XIII can exist in the form of tautomeric isomers. All of the tautomers are represented by Formulas I through XIII, and are intended to be a part of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use in the treatment of at risk populations such as those with impaired glucose tolerance, to prevent or delay the onset of NIDDM and complications arising therefrom, the compounds utilized in the pharmaceutical methods of this invention are administered along with a pharmaceutically acceptable carrier at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compounds of Formulas I through XIII are valuable agents in returning an individual to a state of glucose tolerance and therefore preventing or delaying the onset of NIDDM. The following illustrates testing to show that compounds have the disclosed activity, using the preferred compound troglitazone.

EXAMPLE 1

In a blinded, randomized, fixed-dose, parallel-group, placebo-controlled, outpatient trial, the effects of the test compound, (+)-5-[[4-[(3,4-dihydro-6-hydroxy-2,5,7,8-tetramethyl-2H-1-benzopyran-2-yl)methoxy]phenyl]methyl]-2,4-thiazolidinedione (troglitazone), was compared with that of a placebo on glucose tolerance and on insulin sensitivity. The trial in impaired glucose tolerance (IGT) included a 2-week screening period and a 12-week treatment period. Fifty-six patients were randomized to treatment with placebo or 400 mg/day of troglitazone. Oral glucose tolerance tests (OGTT) and frequently sampled intravenous glucose tolerance tests (FSIGTT) to assess insulin sensitivity were performed before study medication, and after 6 weeks and after 12 weeks of randomized treatment.

Patients included in this study were adults in reasonably good health who have IGT by the WHO criteria as demonstrated by OGTT (Harris M. I., Hadden W. C., Knowler W. C., Berrett P. H., International Criteria for the Diagnosis of Diabetes and Impaired Glucose Tolerance, *Diabetes Care* 1985;8(6):562–7). Most of the patients that were recruited were relatives of patients with NIDDM, patients with a history of gestational diabetes mellitus, patients with a history of prior abnormal OGTT, or patients with other indicators of insulin resistance (coronary artery disease, obesity, hypertriglyceridemia, and hypertension).

The OGTT was carried out according to the following procedure:

Test was administered in the morning after a 10- to 14-hour fast. Water, but not coffee, could be consumed during the fast. Patients were required to remain seated during the test. Study medication was omitted on the morning of the test and taken with lunch.

5 mL of venous blood was collected into a serum separation tube for baseline.

1.75-g/kg body weight, up to a maximum of 75 g of glucose was administered orally as a liquid beverage to be consumed over no more than 5 minutes.

5 mL of venous blood was collected into a serum separation tube every 30 minutes up to 2 hours, timing from the start of ingestion of the glucose.

Each blood specimen was allowed to clot for 30 minutes. The specimens were centrifuged until clot and serum were separated by a well-formed polymer barrier. Serum was transferred from each specimen, using separate pipettes for each, into plastic vials and frozen immediately. If centrifuging of specimens was delayed for any reason, specimens were refrigerated and centrifuged as soon as possible.

Frozen specimens were examined for oral glucose tolerance according to the WHO diagnostic criteria.

| | WHO Diagnostic Criteria | | |
|---|---|---|---|
| Serum Glucose mg/dL (mmol/L) | Normal | IGT | Diabetes |
| Fasting | <140 (<7.8) | <140 (<7.8) | ≧140 (≧7.8) |
| 2 hour | <140 (<7.8) | 140–199 (7.8–11.1) | ≧200 (≧11.1) |

| PROTOCOL 1 Treatment Effects | | | |
|---|---|---|---|
| | 2-hour Glucose (mg/dL) | | Fasting Insulin (UIU/mL) |
| | Baseline | 6 Week | Baseline | 6 Week |

| | Baseline | 6 Week | Baseline | 6 Week |
|---|---|---|---|---|
| Test Compound A | | | | |
| 1 | 167.00 | 81.00 | 14.40 | 2.00 |
| 2 | 143.00 | 146.00 | 9.10 | 25.70 |
| 3 | 143.00 | 106.00 | 4.00 | 6.20 |
| 4 | 167.00 | 85.00 | 12.70 | 11.30 |
| 5 | 166.00 | 113.00 | 13.20 | 13.30 |
| 6 | 158.00 | 101.00 | 20.00 | 11.30 |
| 7 | 148.00 | 81.00 | 8.30 | 2.00 |
| 8 | 166.00 | 172.00 | 21.80 | 9.30 |
| 9 | 187.00 | 158.00 | 22.50 | 12.20 |
| 10 | 147.00 | 98.00 | 12.00 | 7.70 |
| Placebo | | | | |
| 1 | 182.00 | 155.00 | 20.70 | 17.20 |
| 2 | 154.00 | 125.00 | 10.30 | 10.90 |
| 3 | 145.00 | 155.00 | 12.30 | 12.10 |
| 4 | 160.00 | 133.00 | 25.90 | 11.60 |
| 5 | 184.00 | 177.00 | 27.70 | 20.20 |
| 6 | 160.00 | 193.00 | 23.90 | 50.30 |
| 7 | 144.00 | 145.00 | 5.50 | 8.60 |
| 8 | 148.00 | 132.00 | 15.40 | 12.20 |
| 9 | 181.00 | 229.00 | 18.10 | 27.70 |
| 10 | 170.00 | 141.00 | 19.80 | 13.50 |

The results of the OGTTs show that treatment with the test compound correlates to reduction of fasting insulin levels and return of glucose tolerance to the normal range for approximately 70% of the subjects. With the exception of one placebo-responder, treatment with placebo does not change significantly the fasting insulin and glucose tolerance profiles.

| PROTOCOL 1 Summary of OGTT Glucose (mg/dL) | | | | |
|---|---|---|---|---|
| Treatment | Hour | Screening (N = 38) | Week 6 (N = 37) | Week 12 (N = 19) |
| Compound A | 0 | 105 | 88 | 95 |
| | 0.5 | 173 | 153 | 157 |
| | 1.0 | 185 | 151 | 162 |
| | 1.5 | 170 | 145 | 152 |
| | 2.0 | 160 | 123 | 131 |
| Placebo | 0 | 102 | 100 | 99 |
| | 0.5 | 169 | 164 | 163 |
| | 1.0 | 184 | 191 | 186 |
| | 1.5 | 176 | 181 | 176 |
| | 2.0 | 162 | 155 | 150 |

These results show that the average value for 2-hour glucose from the OGTT returns to the normal range for patients treated for 6 weeks and 12 weeks with Test Compound A compared to placebo which shows no significant change in the average value for 2-hour glucose.

| PROTOCOL 1 Conversion After 6 Weeks of Treatment From IGT to Normal by WHO Classification | | |
|---|---|---|
| Treatment | IGT at Screening | Converted to Normal |
| Compound A | 18 | 12 (67%) |
| Placebo | 19 | 7 (37%) |

The results show that on a patient-by-patient analysis, significantly more persons classified with IGT convert to normal glucose tolerance after treatment with Test Compound A (67%) than with placebo (37%).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treating impaired glucose tolerance in order to prevent or delay the onset of noninsulin-dependent diabetes mellitus comprising administering to a host suffering therefrom a therapeutically effective amount of a compound of Formula I:

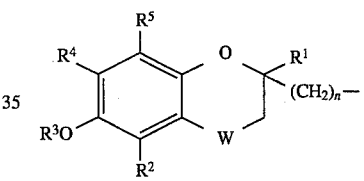

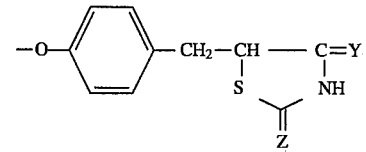

wherein $R^1$ and $R^2$ are the same or different and each represents a hydrogen atom or a $C_1$–$C_5$ alkyl group;

$R^3$ represents a hydrogen atom, a $C_1$–$C_6$ aliphatic acyl group, an alicyclic acyl group, an aromatic acyl group, a heterocyclic acyl group, an aralphatic acyl group, a ($C_1$–$C_6$ alkoxy)carbonyl group, or an aralkyloxycarbonyl group;

$R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group;

n is 1, 2, or 3;

W represents the —$CH_2$—, >CO, or CH—$OR^{6'}$ group (in which $R^{6'}$ represents any 1 of the atoms or groups defined for $R^3$ and may be the same as or different from $R^3$); and Y and Z are the same or different and each represents an oxygen atom or an imino (=NH) group;

and pharmaceutically acceptable salts thereof.

2. A method of treating impaired glucose tolerance in order to prevent or delay the onset of noninsulin-dependent diabetes mellitus comprising administering a therapeutically effective amount of a compound according to claim 1 in admixture with a pharmaceutically acceptable excipient, diluent, or carrier.

3. A method of claim 2 comprising administering to the host suffering therefrom a therapeutically effective amount of a compound of Formula I wherein Y and Z are oxygen.

4. A method of claim 2 comprising administering to the host suffering therefrom a therapeutically effective amount of a compound of Formula I wherein W is —$CH_2$—.

5. A method of claim 2 comprising administering to the host suffering therefrom a therapeutically effective amount of a compound of Formula I wherein n is 1.

6. A method of claim 2 comprising administering to the host suffering therefrom a therapeutically effective amount of a compound of Formula I wherein $R_1$, $R_2$, $R_4$, and $R_5$ are lower alkyl and $R_3$ is H.

7. A method of claim 2 comprising administering to the host suffering therefrom a therapeutically effective amount of a compound of Formula I wherein Z and Y are oxygen, n is 1, and W is —$CH_2$—.

8. A method of claim 2 comprising administering to the host suffering therefrom a therapeutically effective amount of a compound of Formula I wherein the compound is (+)-5-[[4-[(3,4-dihydro-6-hydroxy- 2,5,7,8-tetramethyl-2H-1-benxopyran-2-yl)methoxy]phenyl]methyl]-2,4-thiazolidinedione.

9. A method of treating impaired glucose tolerance to prevent or delay the onset of noninsulin-dependent diabetes mellitus comprising administering to a host suffering therefrom a therapeutically effective amount of a compound of Formula II:

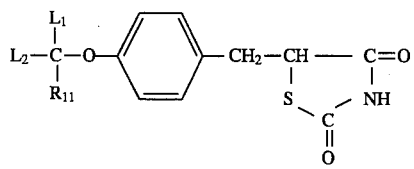

wherein $R_{11}$ is substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula

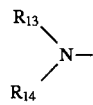

wherein $R_{13}$ and $R_{14}$ are the same or different and each is lower alkyl or $R_{13}$ and $R_{14}$ are combined to each other either directly or as interrupted by a heteroatom selected from the group consisting of nitrogen, oxygen, and sulfur to form a 5- or 6-membered ring;

wherein $R_{12}$ means a bond or a lower alkylene group; and wherein $L_1$ and $L_2$ are the same or different and each is hydrogen or lower alkyl or $L_1$ and $L_2$ are combined to form an alkylene group, or a pharmaceutically acceptable salt thereof.

10. A method of treating impaired glucose tolerance to prevent or delay the onset of noninsulin-dependent diabetes mellitus comprising administering a therapeutically effective amount of a compound according to claim 9 in admixture with a pharmaceutically acceptable excipient, diluent, or carrier.

11. A method of claim 10 comprising administering to the host suffering therefrom a therapeutically effective amount of a compound of Formula II wherein the compound is pioglitazone.

12. A method of claim 10 comprising administering to the host suffering therefrom a therapeutically effective amount of a compound of Formula II wherein the compound is ciglitazone.

13. A method of treating impaired glucose tolerance to prevent or delay the onset of noninsulin-dependent diabetes mellitus comprising administering to a host suffering therefrom a therapeutically effective amount of a compound of Formula III:

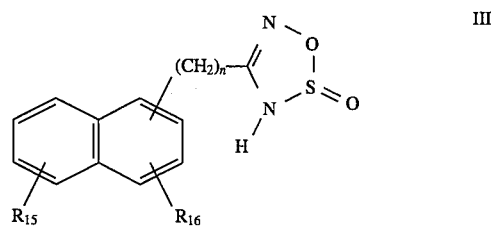

wherein $R_{15}$ and $R_{16}$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro, or halogen substituted benzyloxy; n is 0 to 4 and the pharmaceutically acceptable salts thereof.

14. A method of treating impaired glucose tolerance to prevent or delay the onset of noninsulin-dependent diabetes mellitus comprising administering to a host suffering therefrom a therapeutically effective amount of a compound of Formula IV:

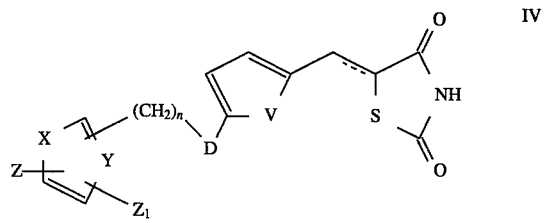

wherein the dotted line represents a bond or no bond;
V is —CH=CH—, —N=CH—, —CH=N— or S;
D is $CH_2$, CHOH, CO, C=$NOR_{17}$ or CH=CH;
X is S, O, $NR_{18}$, —CH=N or —N=CH;
Y is CH or N;
Z is hydrogen, ($C_1$–$C_7$) alkyl, ($C_3$–$C_7$)cycloalkyl, phenyl, naphthyl, pyridyl, furyl, thienyl, or phenyl mono- or disubstituted with the same or different groups which are ($C_1$–$C_3$)alkyl, trifluoromethyl, ($C_1$–$C_3$)alkoxy, fluoro, chloro, or bromo;
Z' is hydrogen or ($C_1$–$C_3$)alkyl;
$R_{17}$ and $R_{18}$ are each independently hydrogen or methyl; and n is 1, 2, or 3;

the pharmaceutically acceptable cationic salts thereof; and the pharmaceutically acceptable acid addition salts thereof when the compound contains a basic nitrogen.

15. A method of treating impaired glucose tolerance to prevent or delay the onset of noninsulin-dependent diabetes mellitus comprising administering to a host suffering therefrom a therapeutically effective amount of a compound of Formula V:

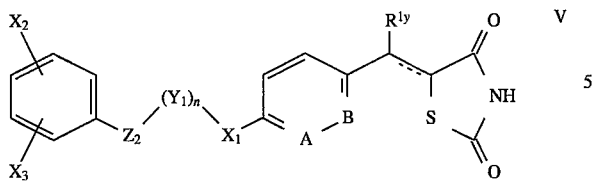

wherein the dotted line represents a bond or no bond;
A and B are each independently CH or N, with the proviso that when A or B is N, the other is CH;
$X_1$ is S, SO, $SO_2$, $CH_2$, CHOH, or CO;
n is 0 or 1;
$Y_1$ is $CHR_{20}$ or $R_{21}$, with the proviso that when n is 1 and $Y_1$ is $NR_{21}$, $X_1$ is $SO_2$ or CO;
$Z_2$ is $CHR_{22}$, $CH_2CH_2$, CH=CH,

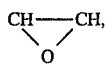

$OCH_2$, $SCH_2$, $SOCH_2$ or $SO_2CH_2$;
$R_{19}$, $R_{20}$, $R_{21}$, and $R_{22}$ are each independently hydrogen or methyl; and
$X_2$ and $X_3$ are each independently hydrogen, methyl, trifluoromethyl, phenyl, benzyl, hydroxy, methoxy, phenoxy, benzyloxy, bromo, chloro, or fluoro;
a pharmaceutically acceptable cationic salt thereof; or
a pharmaceutically acceptable acid addition salt thereof when A or B is N.

16. A method of treating impaired glucose tolerance to prevent or delay the onset of noninsulin-dependent diabetes mellitus comprising administering to a host suffering therefrom a therapeutically effective amount of a compound of Formula VI:

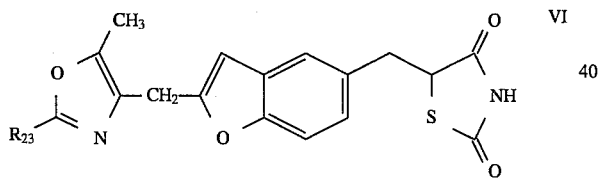

or a pharmaceutically acceptable salt thereof wherein $R_{23}$ is alkyl of 1 to 6 carbon atoms, cycloalkyl of 3 to 7 carbon atoms, phenyl, or mono- or disubstituted phenyl wherein said substituents are independently alkyl of 1 to 6 carbon atoms, alkoxy of 1 to 3 carbon atoms, halogen, or trifluoromethyl.

17. A method of treating impaired glucose tolerance to prevent or delay the onset of noninsulin-dependent diabetes mellitus comprising administering to a host suffering therefrom a therapeutically effective amount of a compound of Formula VII:

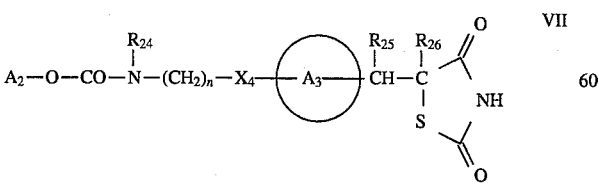

or a tautomeric form thereof and/or a pharmaceutically acceptable salt thereof, and/or a pharmaceutically acceptable solvate thereof, wherein:

$A_2$ represents an alkyl group, a substituted or unsubstituted aryl group, or an aralkyl group wherein the alkylene or the aryl moiety may be substituted or unsubstituted;
$A_3$ represents a benzene ring having in total up to 3 optional substituents;
$R_{24}$ represents a hydrogen atom, an alkyl group, an acyl group, an aralkyl group wherein the alkyl, or the aryl moiety may be substituted or unsubstituted, or a substituted or unsubstituted aryl group; or $A_2$ together with $R_{24}$ represents substituted or unsubstituted $C_{2-3}$ polymethylene group, optional substituents for the polymethylene group being selected from alkyl or aryl or adjacent substituents together with the methylene carbon atoms to which they are attached form a substituted or unsubstituted phenylene group;
$R_{25}$ and $R_{26}$ each represent hydrogen, or $R_{25}$ and $R_{26}$ together represent a bond;
$X_4$ represents O or S; and
n represents an integer in the range of from 2 to 6.

18. A method of treating impaired glucose tolerance to prevent or delay the onset of noninsulin-dependent diabetes mellitus comprising administering to a host suffering therefrom a therapeutically effective amount of a compound of Formula VIII in unit dosage form

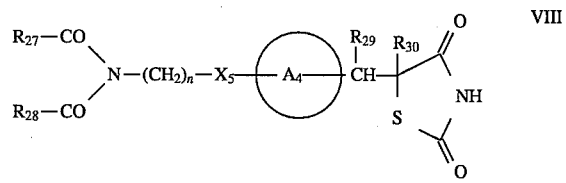

or a tautomeric form thereof and/or a pharmaceutically acceptable salt thereof, and/or a pharmaceutically acceptable solvate therefor, wherein:

$R_{27}$ and $R_{28}$ each independently represent an alkyl group, a substituted or unsubstituted aryl group, or an aralkyl group being substituted or unsubstituted in the aryl or alkyl moiety;
or $R_{27}$ together with $R_{28}$ represents a linking group, the linking group consisting of an optionally substituted methylene group and either a further optionally substituted methylene group or an O or S atom, optional substituents for the said methylene groups being selected from alkyl-, aryl, or aralkyl, or substituents of adjacent methylene groups together with the carbon atoms to which they are attached form a substituted or unsubstituted phenylene group;
$R_{29}$ and $R_{30}$ each represent hydrogen, or $R_{29}$ and $R_{30}$ together represent a bond;
$A_4$ represents a benzene ring having in total up to 3 optional substituents;
$X_5$ represents O or S; and
n represents an integer in the range of from 2 to 6.

19. A method of treating impaired glucose tolerance to prevent or delay the onset of noninsulin-dependent diabetes mellitus comprising administering to a host suffering therefrom a therapeutically effective amount of a compound of Formula IX:

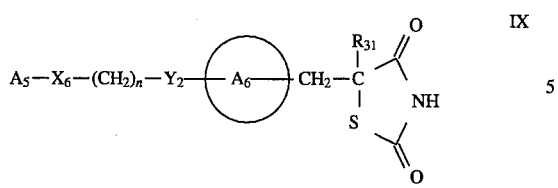

or a tautomeric form thereof and/or a pharmaceutically acceptable salt thereof, and/or a pharmaceutically acceptable solvate thereof, wherein:

$A_5$ represents a substituted or unsubstituted aromatic heterocyclyl group;

$A_6$ represents a benzene ring having in total up to 5 substituents;

$X_6$ represents O, S, or $NR_{32}$ wherein $R_{32}$ represents a hydrogen atom, an alkyl group, an acyl group, an aralkyl group, wherein the aryl moiety may be substituted or unsubstituted, or a substituted or unsubstituted aryl group;

$Y_2$ represents O or S;

$R_{31}$ represents an alkyl, aralkyl, or aryl group; and n represents an integer in the range of from 2 to 6.

20. A method of treating impaired glucose tolerance to prevent or delay the onset of noninsulin-dependent diabetes mellitus comprising administering to a host suffering therefrom a therapeutically effective amount of a compound of Formula X:

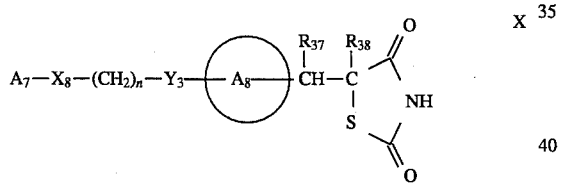

or a tautomeric form thereof and/or a pharmaceutically acceptable salt thereof, and/or a pharmaceutically acceptable solvate thereof, wherein:

$A_7$ represents a substituted or unsubstituted aryl group;

$A_8$ represents a benzene ring having in total up to 5 substituents;

$X_8$ represents O, S, or $NR_{39}$ wherein $R_{39}$ represents a hydrogen atom, an alkyl group, an acyl group, an aralkyl group, wherein the aryl moiety may be substituted or unsubstituted, or a substituted or unsubstituted aryl group;

$Y_3$ represents O or S;

$R_{37}$ represents hydrogen;

$R_{38}$ represents hydrogen or an alkyl, aralkyl, or aryl group or $R_{37}$ together with $R_{38}$ represents a bond; and n represents an integer in the range of from 2 to 6.

21. A method of treating impaired glucose tolerance to prevent or delay the onset of noninsulin-dependent diabetes mellitus comprising administering to a host suffering therefrom a therapeutically effective amount of a compound of Formula XI:

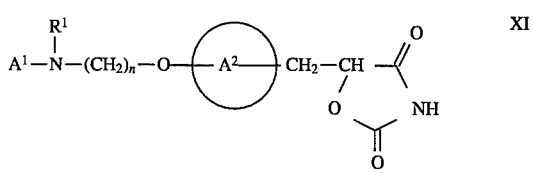

or a tautomeric form thereof and/or a pharmaceutically acceptable salt thereof, and/or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to five substitutents; and n represents an integer in the range of from 2 to 6.

22. A method of treating impaired glucose tolerance to prevent or delay the onset of noninsulin-dependent diabetes mellitus comprising administering to a host suffering therefrom a therapeutically effective amount of a compound of Formula XII or XIII:

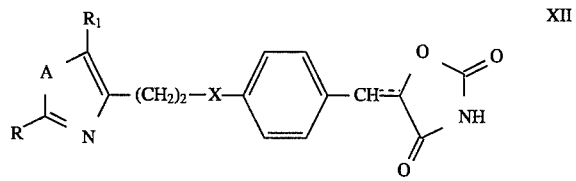

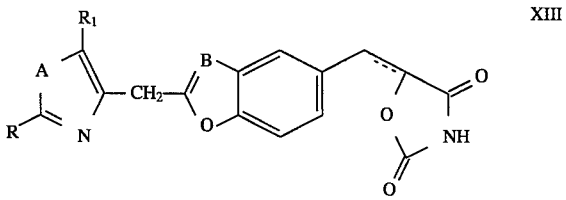

or a pharmaceutically acceptable salt thereof wherein the dotted line represents a bond or no bond; R is cycloalkyl of three to seven carbon atoms, naphthyl, thienyl, furyl, phenyl or substituted phenyl wherein said substituent is alkyl of one to three carbon atoms, alkoxy of one to three carbon atoms, trifluoromethyl, chloro, fluoro or bis(trifluoromethyl); $R_1$ is alkyl of one to three carbon atoms; X is O or C=O; A is O or S; and B is N or CH.

23. A method of treating impaired glucose tolerance to prevent or delay the onset of noninsulin-dependent diabetes mellitus comprising administering to a host suffering therefrom a therapeutically effective amount of a compound selected from the group consisting of (+)-5-[[4-[(3,4-dihydro-6-hydroxy-2,5,7,8-tetramethyl-2H-1-benzopyran-2-yl)methoxy]phenyl]methyl]-2,4-thiazolidinedione: (troglitazone);

4-(2-naphthylmethyl)-1,2,3,5-oxathiadiazole-2-oxide;

5-[4-[2-[N-(benzoxazol-2-yl)-N-methylamino]ethoxy]benzyl]-5-methylthiazolidine-2,4-dione;

5-[4-[2-[2,4-dioxo-5-phenylthiazolidin-3-yl)ethoxy]benzyl] thiazolidine-2,4-dione;

5-[4-[2-[N-methyl-N-(phenoxycarbonyl)amino]ethoxy]benzyl] thiazolidine-2,4-dione;

5-[4-(2-phenoxyethoxy)benzyl]thiazolidine-2,4-dione;

5-[4-[2-(4-chlorophenyl)ethylsulfonyl]benzyl] thiazolidine-2,4-dione;
5-[4-[3-(5-methyl-2-phenyloxazol-4-yl)propionyl]benzyl]thiazolidine-2,4-dione;
5-[4-[(1-methylcyclohexyl)methoxy]benzyl]thiadiazolidine-2,4-dione: (ciglitazone);
5-[[4-(3-hydroxy-1-methylcyclohexyl)methoxy]benzyl]thiadiazolidine-2,4-dione;
5-[4-[2-(5-methyl-2-phenyloxazol-4-yl)ethoxyl]benzyl]thiadizolidione-2,4-dione;
5-[4-[2-(5-ethylpyridin-2-yl)ethoxyl]benzyl]thiadiazolidine-2,4-dione: (pioglitazone);
5-[(2-benzyl-2,3-dihydrobenzopyran)-5-ylmethyl]thiadiazoline-2,4-dione: (englitazone);
5-[[2-(2-naphthylmethyl)benzoxazol]-5-ylmethyl]thiadiazoline-2,4-dione;
5-[4-[2-(3-phenylureido)ethoxyl]benzyl]thiadiazoline-2,4-dione;
5-[4-[2-[N-(benzoxazol-2-yl)-N-methylamino]ethoxy]benzy]thiadiazoline-2,4-dione;
5-[4-[3-(5-methyl-2-phenyloxazol-4-yl)propionyl]benzyl]thiadiazoline-2,4-dione;
5-[2-(5-methyl-2-phenyloxazol-4-ylmethyl)benzofuran-5-ylmethyl]-oxazolidine-2,4-dione;
5-[4-[2-[N-methyl-N-(2-pyridyl)amino]ethoxy]benzyl]thiazolidine-2,4-dione; and
5-[4-[2-[N-(benzoxazol-2-yl)-N-methylamino]ethoxy]benzyl]-oxazolidine-2,4-dione.

* * * * *

UNITED STATES PATENT AND TRADEMARK OFFICE
CERTIFICATE OF CORRECTION

PATENT NO. : 5,478,852
DATED : December 26, 1995
INVENTOR(S) : Olefsky et al

Page 1 of 2

It is certified that error appears in the above-indentified patent and that said Letters Patent is hereby corrected as shown below:

Column 28, line 14, after "zyl]-oxazolidine-2,4-dione.", add the following claims:

--24. The method of treating impaired glucose tolerance of claim 23 wherein said compound is (+)-5-[[4-[(3,4-dihydro-6-hydroxy-2,5,7,8-tetramethyl-2H-1-benzopyran-2-yl)methoxy]-phenyl]methyl]-2,4-thiazolidinedione: (troglitazone).

25. The method of treating impaired glucose tolerance of claim 23 wherein said compound is 5-[4-[2-(5-ethylpyridin-2-yl)ethoxyl]benzyl]-thiadiazolidine-2,4-dione: (pioglitazone).

26. The method of treating impaired glucose tolerance of claim 23 wherein said compound is 5-[(2-benzyl-2,3-dihydrobenzopyran)-5-ylmethyl]-thiadiazoline-2,4-dione: (englitazone).

UNITED STATES PATENT AND TRADEMARK OFFICE
CERTIFICATE OF CORRECTION

PATENT NO. : 5,478,852
DATED : December 26, 1995
INVENTOR(S) : Olefsky et al

It is certified that error appears in the above-indentified patent and that said Letters Patent is hereby corrected as shown below:

27.  The method of treating impaired glucose tolerance of claim 23 wherein said compound is 5-[4-[2-[N-methyl-N-(2-pyridyl)amino]ethoxy]-benzyl]thiazolidine-2,4-dione.--.

Signed and Sealed this

Fourteenth Day of July, 1998

Attest:

BRUCE LEHMAN

*Attesting Officer*       *Commissioner of Patents and Trademarks*

US005478852C1

(12) REEXAMINATION CERTIFICATE (4289th)
United States Patent
Olefsky et al.

(10) Number: US 5,478,852 C1
(45) Certificate Issued: Mar. 13, 2001

(54) USE OF THIAZOLIDINEDIONE DERIVATIVES AND RELATED ANTIHYPERGLYCEMIC AGENTS IN THE TREATMENT OF IMPAIRED GLUCOSE TOLERANCE IN ORDER TO PREVENT OR DELAY THE ONSET OF NONINSULIN-DEPENDENT DIABETES MELLITUS

(75) Inventors: Jerrold Olefsky, Solano Beach, CA (US); Tammy Antonucci, Mequon, WI (US); Dean Lockwood, Ann Arbor; Rebecca Norris, Kewadin, both of MI (US)

(73) Assignee: Sankyo Company, Limited, Tokyo (JP)

Reexamination Request:
No. 90/005,547, Nov. 4, 1999

Reexamination Certificate for:
Patent No.: 5,478,852
Issued: Dec. 26, 1995
Appl. No.: 08/293,899
Filed: Aug. 23, 1994

Certificate of Correction issued Jul. 14, 1998.

Related U.S. Application Data

(63) Continuation-in-part of application No. 08/122,251, filed on Sep. 15, 1993, now abandoned.
(51) Int. Cl.$^7$ .................. A61K 31/41; A61K 31/422; A61K 31/426; A61K 31/427; A61K 31/4439
(52) U.S. Cl. .................. 514/342; 514/255.05; 514/256; 514/360; 514/369; 514/375; 514/376
(58) Field of Search .................. 514/255.05, 256, 514/342, 360, 369, 375, 376

(56) References Cited

PUBLICATIONS

Bodkin, , N.L., et. al. Hepatic Glucose Production and Insulin Sensitivity Preceding Diabetes in Monkeys; *Am. J. Physio.*, vol. 256 (Endocrinol. Metab.), pp. E676–E881, 1989.

Bressler, Rubin; Johnson, David; New Pharmacological Approaches to Therapy of NIDDM; *Diabetes Care;* vol. 15, No. 6, pp. 792–805, Jun. 1992.

Ciaraldi, Theodore P., et. al. In Vitro Studies on the Action of CS–045, a New Antidiabetic Agent; *Metabolism,* vol. 3, No. 10, pp. 1056–1062, 1990.

Colca, J.R.; Morton, D.R.; Chapter 24: Antihyperglycemic Thiazolidinediones: Ciglitizone and its Analogues; *New Antidiabetic Drugs*, pp. 255–261 (Smith–Gordon, 1990.).

Colca, J.R. et al. Ciglitazone, A Hypoglycemic Agent: Early Effects on the Pancreatic Islets of Ob/Ob Mice; *Metabolism Clinical and Experimental;* vol. 37, No. 3, pp. 276–280, Mar. 1998.

Colca, Jerry R.; Tanis, Steven P.; Ch. 23: Recent Advances in the Discovery and Development of Potential Antidiabetic Agents: *Annual Reports in Medicinal Chemistry Volume 27;* pp. 219–226 (Academic Press, Inc., 1992.).

DeFronzo, Ralph A., et. al. Fasting Hyperglycemia in Non–insulin–dependent Diabetes Mellitus: Contributions of Excessive Hepatic Glucose Production and Impaired Tissue Glucose Uptake; *Metabolism,* vol. 38, No. 4, pp. 387–395, 1989.

DeFronzo, Ralph A. et al. Pathogenesis of NIDDM: A Precarious Balance Between Insulin Action and Insulin Secretion; *International Textbook of Diabetes Mellitus,* pp. 569–633 (John Wiley & Sons, Ltd. 1992).

DeFronzo, Ralph A. The Triumvirate: β–Cell, Muscle, Liver; A Collusion Responsible for NIDDM; *Diabetes,* vol. 37, pp. 667–687, Jun. 1988.

Diani, A.R. et. al. Ciglitazone, a New Hyopglycaemic Agent. 4. Effect on Pancreatic Islets of C57BL/6J–ob/ob and C57BL/KsJ–db/db Mice, *Diabetologia,* vol. 27, pp. 225–234, 1984.

Erikkson, J., et. al. Early Metabolic Defects in Persons at Increased Risk for Non–insulin–dependent Diabetes; *New England Journal of Medicine,* vol. 321, No. 6, pp. 337–343, 1989.

Eriksson, K.F. et al. Prevention of Type 2 (non–insulin dependent) Diabetes Mellitus by Diet & Physical Exercise—The 6–Year Malmo Feasibility Study; *Diabetologia,* vol. 34, pp. 891–898, 1991.

Fajans, Stefan S. *Classification and Diagnosis of Diabetes,* pp. 357–372.

Felber, Jean–Pierre et al. Role of Lipid Oxidation in Pathogenesis of Insulin Resistance of Obesity and Type II Diabetes; *Diabetes;* vol. 35, pp. 1341–1350, Nov. 1987.

Fery, Francois Role of Hepatic Glucose Production and Glucose Uptake in Pathogenesis of Fasting Hyperglycemia in Type 2 Diabetes: Normalization of Glucose Kinetics by Short–Term Fasting; *Journal of Clinical Endocrinology and Metabolism,* vol. 78, No. 3, pp. 536–542, 1994.

Haffner, Steven M. et al. Hyperinsulinemia in a Population at High Risk for Non–Insulin–Dependent Diabetes Mellitus; *The New England Journal of Medicine;* vol. 315, No. 4, pp. 220–224, 1986.

Haffner, Steven M. et al. Incidence of Type II Diabetes in Mexican Americans Predicted by Fasting Insulin Glucose Levels, Obesity, and Body Fat Distribution; *Diabetes;* vol. 39, No. 3, pp. 283–288, Mar. 1990.

Hansen, B.C., et. al. Heterogeneity of Insulin Responses: Phases Leading to Type 2 (non–insulin–dependent) Diabetes Mellitus in the Rhesus Monkey, *Diabetologia,* vol. 29, pp. 713–719, 1986.

Hofmann, Cecilia et al. Glucose Transport Deficiency in Diabetic Animals Is Corrected By Treatment with The Oral Antihyperglycemic Agent Pioglitazone; *Endocrinology,* vol. 129, No. 4, pp. 1915–1925, 1991.

(List continued on next page.)

Primary Examiner—Richard L. Raymond

(57) ABSTRACT

Novel methods of using thiazolidinone derivatives and related antihyperglycemic agents to treat populations experiencing impaired glucose intolerance in order to prevent or delay the onset of noninsulin-dependent diabetes mellitus (NIDDM) and complications arising therefrom are disclosed.

OTHER PUBLICATIONS

Hofmann, Cecilia A.; Colca, Jerry R.; New Oral Thiazolidinedione Antidiabetic Agents Act as Insulin Sensitizers; *Diabetes Care,* vol. 15, No. 8, pp. 1075–1078, Aug. 1992.

King, H. et al. The Natural History of Impaired Glucose Tolerance in the Micronesian Population of Nauru: A Six–Year Follow–Up Study; *Diabetologia,* vol. 26, pp. 39–43, 1984.

Knowler, William C. et al. Diabetes Mellitus in the Pima Indians: Incidence, Risk Factors and Pathogenesis; *Diabetes /Metabolism Reviews,* pp. 1–27, 1990.

Kraegen, E.W. et al. Effects of BRL49653 in Normal and Insulin Resistant (High–Fat–Fed) Rats: New Information on the Mode of Action of Thiazolidinediones; *Diabetes,* $53^{rd}$ Annual Meeting, Abstract Book, p. 257, Jun. 12–15, 1993.

Lillioja, Steven et al. Impaired Glucose Tolerance as a Disorder of Insulin Action; *The New England Journal of Medicine,* vol. 318, No. 19, pp. 1217–1225, May 12, 1988.

Lillioja, Stephen et al. Insulin Resistance And Insulin Secretory Dysfunction as Precursors of Non–Insulin–Dependent Diabetes Mellitus; *The New England Journal of Medicine,* vol. 329, No. 27, pp. 1988–1992, Dec. 30, 1993.

Minton, et al. Acute Pharmacodynamic Effects of GR92132X, a Thiazolidinedione, in Healthy Subjects; *Diabetic Medicine,* vol. 10, Supp., p. S14, 1993.

Myers, et al. Tanabe 174 (TA174, LY282249), a Novel Thiazolidinedione, Enhances Insulin Sensitivity in the Normal Dog; *Diabetes,* vol. 42, Supp. 1, A256, Jun. 12–15, 1993.

National Institute of Diabetes and Digestive and Kidney Diseases; Request for Applications No. DK–93–007 (Full Text), *NIH Guide 1993,* vol. 22, No. 18, pp. 14–16, 1993.

Reaven, Gerald M.; Role of Insulin Resistance in Human Disease (Syndrome X): An Expanded Definition; *Annu. Rev. Med.,* vol. 44, pp. 121–131, 1993.

Saad, Mohammed et al. The Natural History of Impaired Glucose Tolerance in the Pima Indians; *The New England Journal of Medicine,* vol. 319, No. 23, pp. 1500–1506, Dec. 8, 1988.

Sartor et al. Ten–Year Follow–up of Subjects with Impaired Glucose Tolerance: Prevention of Diabetes by Tolbutamide and Diet Regulation; *Diabetes,* vol. 29, pp. 41–49, Jan. 1980.

Scheen, A.J.; Lefebvre, P.J.; Pharmacological Treatment of the Obese Diabetic Patient; *Diabetes & Metabolism,* vol. 19, No. 6, pp. 547–559, 1993.

Shulman, Gerald I., et. al. Quantitation of Muscle Gylcogen Synthesis in Normal Subjects and Subjects with Non–Insulin–Dependent Diabetes by $^{13}C$ Nuclear Magnetic Resonance Spectroscopy, *New England Journal of Medicine,* vol. 322, No. 25, Jan. 25, 1990.

Stern, Michael P., et. al. Stability Over Time of Modern Diagnostic Criteria for Type 2 Diabetes; *Diabetes Care,* vol. 16, No. 7, pp. 978–983, 1993.

Stevenson, Ralph W. et al. Antidiabetic Agent Englitazone Enhances Insulin Action in Nondiabetic Rats Without Producing Hypoglycemia; *Metabolism,* vol. 40, No. 12, pp. 1268–1274, Dec. 1991.

Suter, Stephan J. et al. Metabolic Effects of New Oral Hypoglycemic Agent CS–045 in NIDDM Subjects; *Diabetes Care,* vol. 15, No. 2, pp. 193–203, 1992.

Vialettes, B.; Silvestre, P.; Pharmacological Approach in the Treatment of Insulin Resistance; *Horm. Res.,* vol. 38, pp. 51–56, 1992.

Warram, James H. et al. Slow Glucose Removal Rate and Hyperinsulinemia Precede the Development of Type II Diabetes in the Offspring of Diabetic Parents; *Annals of Internal Medicine,* vol. 113, pp. 909–915, 1990.

Widen, Elisabeth I.M. et al. Metformin Normalizes Nonoxidative Glucose Metabolism in Insulin–Resistant Normoglycemic First–Degree Relatives of Patients With NIDDM; *Diabetes,* vol. 41, No. 3, pp. 354–358, Mar. 1992.

Zimmet, P.Z. et al. Hyperinsulinaemia in Youth is a Predictor of Type 2 (Non–Insulin–Dependent) Diabetes Mellitus; *Diabetologia,* vol. 35, No. 6, pp. 534–541, Jun. 1992.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–27 is confirmed.

\* \* \* \* \*

(12) EX PARTE REEXAMINATION CERTIFICATE (5198th)
United States Patent
Olefsky et al.

(10) Number: US 5,478,852 C2
(45) Certificate Issued: Sep. 6, 2005

(54) USE OF THIAZOLIDINEDIONE DERIVATIVES AND RELATED ANTIHYPERGLYCEMIC AGENTS IN THE TREATMENT OF IMPAIRED GLUCOSE TOLERANCE IN ORDER TO PREVENT OR DELAY THE ONSET OF NONINSULIN-DEPENDENT DIABETES MELLITUS

(75) Inventors: Jerrold Olefsky, Solano Beach, CA (US); Tammy Antonucci, Mequon, WI (US); Dean Lockwood, Ann Arbor, MI (US); Rebecca Norris, Kewadin, MI (US)

(73) Assignee: Sankyo Company, Limited, Tokyo (JP)

Reexamination Request:
No. 90/006,062, Jul. 19, 2001
No. 90/006,599, Apr. 14, 2003

Reexamination Certificate for:
Patent No.: 5,478,852
Issued: Dec. 26, 1995
Appl. No.: 08/293,899
Filed: Aug. 23, 1994

Reexamination Certificate B1 5,478,852 issued Mar. 13, 2001.

Certificate of Correction issued Jul. 14, 1998.

Related U.S. Application Data

(63) Continuation-in-part of application No. 08/122,251, filed on Sep. 15, 1993, now abandoned.

(51) Int. Cl.$^7$ .......................... A61P 3/10; A61K 31/44; A61K 31/425; A61K 31/41
(52) U.S. Cl. .................. 514/369; 514/256; 514/342; 514/360; 514/375; 514/376; 514/252
(58) Field of Search .................... 514/252, 256, 514/342, 360, 369, 375, 376

(56) References Cited

PUBLICATIONS

Reinauer et al. (Laboratory Diagnosis and Monitoring of Diabetes Mellitus, World Health Organization (2002).*

Ikeda et al. (Arzneimittel–Forshung Drug research, 40 (1), pp. 156–162 (1990).*

Kemnitz et al. (Pioglitazone Reduces Insulin Levels and Blood Pressure in Obese Rhesus Monkeys, Third International Symp., Hypertention Associated with Diabetes Mellitus, 1991).*

Bodkin et al. (Am. J. of Phys., Endocrinology and Metabolism, 19 (5): pp. E676–E681 (1989)).*

* cited by examiner

*Primary Examiner*—Bruck Kifle

(57) ABSTRACT

Novel methods of using thiazolidinone derivatives and related antihyperglycemic agents to treat populations experiencing impaired glucose intolerance in order to prevent or delay the onset of noninsulin-dependent diabetes mellitus (NIDDM) and complications arising therefrom are disclosed.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–22 is confirmed.

Claims 23 and 25–26 are determined to be patentable as amended.

Claims 24 and 27, dependent on an amended claim, are determined to be patentable.

New claim 28 is added and determined to be patentable.

23. A method of treating impaired glucose tolerance to prevent or delay the onset of noninsulin-dependent diabetes mellitus comprising administering to a host suffering therefrom a therapeutically effective amount of a compound selected from the group consisting of (+)-5-[[4-[(3,4-dihydro-6-hydroxy-2,5,7,8-tetramethyl-2H-1-benzopyran-2-yl)methoxy]phenyl]methyl]-2,4-thiazolidinedione: (troglitazone);

4-(2-naphthylmethyl)-1,2,3,5-oxathiadiazole-2-oxide;

5-[4-[2-[N-(benzoxazol-2-yl)-N-methylamino]ethoxy]benzyl]-5-methylthiazolidine-2,4-dione;

5-[4-[2-[2,4-dioxo-5-phenylthiazolidin-3-yl)ethoxy]benzyl]thiazolidine-2,4-dione;

5-[4-[2-[N-methyl-N-(phenoxycarbonyl)amino]ethoxy]benzyl]thiazolidine-2,4-dione;

5-[4-(2-phenoxyethoxy)benzyl]thiazolidine-2,4-dione;

5-[4-[2-(4-chlorophenyl)ethylsulfonyl]benzyl]thiazolidine-2,4-dione;

5-[4-[3-(5-methyl-2-phenyloxazol-4-yl)propionyl]benzyl]thiazolidine-2,4-dione;

5-[4-[(1-methylcyclohexyl)methoxy]benzyl]thiadiazolidine-2,4-dione: (ciglitazone);

5-[[4-(3-hydroxy-1-methylcyclohexyl)methoxy]benzyl]thiadiazolidine-2,4-dione;

5-[4-[2-(5-methyl-2-phenyloxazol-4-yl)ethoxyl]benzyl]thiadizolidione-2,4-dione;

[5-[4-[2-(5-ethylpyridin-2-yl)ethoxyl]benzyl]thiadiazolidine-2,4-dione: (pioglitazone);

5-[(2-benzyl-2,3-dihydrobenzopyran)-5-ylmethyl]thiadiazoline-2,4-dione: (englitazone);]

5-[[2-(2-naphthylmethyl)benzoxazol]-5-ylmethyl]thiadiazoline-2,4-dione;

5-[4-[2-(3-phenylureido)ethoxyl]benzyl]thiadiazoline-2,4-dione;

5-[4-[2-[N-(benzoxazol-2-yl)-N-methylamino]ethoxy]benzyl]thiadiazoline-2,4-dione;

5-[4-[3-(5-methyl-2-phenyloxazol-4-yl)propionyl]benzyl]thiadiazoline-2,4-dione;

5-[2-(5-methyl-2-phenyloxazol-4-ylmethyl)benzofuran-5-ylmethyl]-oxazolidine-2,4-dione;

5-[4-[2-[N-methyl-N-(2-pyridyl)amino]ethoxy]benzyl]thiazolidine-2,4-dione; and

5-[4-[2-[N-(benzoxazol-2-yl)-N-methylamino]ethoxy]benzyl]-oxazolidine-2,4-dione.

25. [The] *A* method of treating impaired glucose tolerance [of claim 23 wherein said compound is] *to prevent or delay the onset of noninsulin-dependent diabetes mellitus comprising administering to a host suffering therefrom a therapeutically effective amount of* 5-[4-[2-(5-ethylpyridin-2-yl)ethoxyl]benzyl]thiadiazolidine-2,4-dione: (pioglitazone).

26. [The] *A* method of treating impaired glucose tolerance [of claim 23 wherein said compound is] *to prevent or delay the onset of noninsulin-dependent diabetes mellitus comprising administering to a host suffering therefrom a therapeutically effective amount of* 5-[(2-benzyl-2,3-dihydrobenzopyran)-5-ylmethyl]thiadiazoline-2,4-dione: (englitazone).

28. *The method of any one of claims 1–26 wherein the host is human.*

* * * * *